(12) United States Patent
Ramani (10) Patent No.: US 10,421,728 B2
(45) Date of Patent: Sep. 24, 2019

(54) PEPTIDE NUCLEIC ACID MONOMER AND A PREPARATION METHOD

(71) Applicant: AMRITA VISHWA VIDYAPEETHAM, Coimbatore (IN)

(72) Inventor: Prasanna Ramani, Coimbatore (IN)

(73) Assignee: AMRITA VISHWA VIDYAPEETHAM, Coimbatore (IN)

( * ) Notice: Subject to any disclaimer, the term of this patent is extended or adjusted under 35 U.S.C. 154(b) by 0 days.

(21) Appl. No.: 16/003,304

(22) Filed: Jun. 8, 2018

(65) Prior Publication Data

US 2018/0354911 A1 Dec. 13, 2018

(51) Int. Cl.
*C07D 239/54* (2006.01)

(52) U.S. Cl.
CPC .................................. *C07D 239/54* (2013.01)

(58) Field of Classification Search
CPC .................................................... C07D 239/54
See application file for complete search history.

(56) References Cited

U.S. PATENT DOCUMENTS

| 5,714,331 A | 2/1998 | Buchardt et al. |
| 5,859,191 A | 1/1999 | Miller et al. |
| 7,022,851 B2 | 4/2006 | Kim et al. |

OTHER PUBLICATIONS

Falkiewicz et al., Synthesis of Achiral and Chiral Peptide Nucleic Acid (PNA) Monomers Using Mitsunobu Reaction, Tetrahedron, vol. 57, No. 37, pp. 7909-7917 (Year: 2001).*
Kosynkina L., et al., "A Convenient Synthesis of Chiral Peptide Nucleic Acid (PNA) Monomers," Tetrahedron Letters, Jul. 18, 1994, vol. 35 (29), pp. 5173-5176.

* cited by examiner

*Primary Examiner* — Brenda L Coleman
(74) *Attorney, Agent, or Firm* — Convergence Intellectual Property Law P.C.; Jonathan Garfinkel (57) ABSTRACT

The disclosure in various embodiments is related to a peptide nucleic acid monomer (VI) and an improved process for preparation of PNA (VI) using nosyl-group containing starting material. The process includes reacting amino acid with a nosyl group. The nosyl protected amino acid is alkylated with 2-(Boc-amino)ethyl bromide to obtain an intermediate. The nosyl group of the obtained intermediate is removed to form a PNA backbone. The PNA backbone upon addition of a modified nucleobase results in the formation of a PNA monomer (VI). The obtained PNA monomer exhibits either chiral or achiral geometric properties.

15 Claims, 7 Drawing Sheets

PEPTIDE NUCLEIC ACID MONOMER AND A PREPARATION METHOD

CROSS-REFERENCES TO RELATED APPLICATIONS

This application claims priority to Indian patent application No. 201741020193, filed on 8 Jun. 2017, the full disclosure of which is incorporated herein by reference.

FIELD OF THE INVENTION

The present invention relates generally to nucleic acids and in particular to monomers of peptide nucleic acid (PNA) and a method of preparation thereof.

DESCRIPTION OF THE RELATED ART

Peptide nucleic acid (PNA) is a bio-molecular tool with broad range of applications. PNAs are considered to be the most important backbone modifications of DNA, which was developed by Nielsen and co-workers, where the entire sugar-phosphate backbone is replaced by a homo-morphous, chiral/achiral and uncharged peptide backbone based on N-(2-aminoethyl) glycine units (aegPNA). The nucleobases are attached to the backbone through a carbomethylene linker. The inter-nucleobases distance in PNA is preserved, allowing its binding to the target DNA/RNA sequences with high sequence specificity and affinity. PNA is considered to be an exact DNA mimic in terms of base-pair recognition. But, PNA has poor solubility compared to both DNA and RNA. Low cellular permeability limits its applications for gene or antisense therapies (via infra). PNAs lacks in probe to recognize the PNA-DNA hybridization event.

U.S. Pat. No. 5,859,191 to Miller et al., discloses a method for the site-specific modification of peptide alpha amines at specific N-alpha positions. The method of modification consists of treating a free terminal alpha amine with an aryl sulfonamide activating agent, to form an activated amide which is deprotonated with a base and modified by the addition of a substituent group.

U.S. Pat. No. 5,714,331 to Buchardt et al., discloses a method to enhance binding affinity, sequence specificity and solubility of PNAs. U.S. Pat. No. 7,022,851 to Kim et al., discloses the preparation of monomers for the preparation of PNA (peptide nucleic acid) oligomers and provides method for the synthesis of both predefined sequence PNA oligomers and random sequence PNA oligomers.

"Synthesis of achiral and chiral peptide nucleic acid (PNA) monomers using "Mitsunobu reaction" Falkiewicz et al., Tetrahedron, 2001 discusses the synthesis of N-, C-protected pseudodipeptides with a reduced peptide bond and a peptide nucleic acid (PNA) monomers, based on the Mitsunobu reaction of N-Boc-β-amino alcohols with N-o-nitrobenzenesulfonyl-protected (oNBS-protected) amino acid esters.

"A convenient synthesis of chiral peptide nucleic acid (PNA) monomers" Kosynkina et al., Tetrahedron Letters, 1994 discusses the preparation of chiral peptide nucleic acid monomers containing amino acid chains from BOC-protected amino acids.

The present disclosure describes a process, which is simple and cheap, for the preparation of chiral or achiral PNA monomers.

SUMMARY OF THE INVENTION

The present disclosure relates to a process for synthesizing peptide nucleic acid (PNA) monomers which forms the building blocks of PNA oligomers.

In various embodiments the process for preparation of a PNA monomer, includes providing a nosyl-group containing starting material of formula (II)

where $R_1$ is —H, —$CH_3$, —$CH(CH_3)_2$, —$CH_2CH(CH_3)_2$, —$CH_2OH$, —$CH_2C_6H_5OH$ and $R_3$ is o-nosyl or p-nosyl.

The nosyl-group containing starting material of formula (II) is alkylated with 2-(Boc-amino) ethyl bromide to form an intermediate of formula (IV)

where $R_2$ in (IV) is an amine-protecting group. The nosyl group is removed to obtain a PNA backbone of formula (V)

A nucleobase is added to (V) to obtain a PNA monomer.

In various embodiments a nosyl-group containing starting material (II) is obtained by a reaction between an amino acid containing a first reaction mixture with nosyl chloride. In one embodiment the first reaction mixture includes dichloro methane and triethyl amine or diisopropyl ethylamine. In one embodiment the reaction is carried out at a temperature between 0-35° C. In some embodiments the nosyl product is obtained by stirring the mixture for 20-30 h.

In various embodiments alkylating includes reacting the nosylated starting material (II) and with a second reaction mixture. Second reaction mixture includes cesium carbonate or 1,8-diazabicyclo[5.4.0] undec-7-ene (DBU), or triethylamine or pyridine and dimethylformamide as solvent. In some embodiments, the alkylation is performed at a temperature between 25-40° C. In some embodiments the alkylation is performed for a period of 10-24 h. In one embodiment the intermediate (IV) is further purified by column chromatography.

In various embodiments, removal of the nosyl group includes deprotecting the nosyl group having a third reaction mixture under nitrogen atmosphere at 0° C. The reaction mixture is stirred at a temperature between 20-30° C. for a period of 15-20 h. In some embodiments the third reaction mixture includes a DMF medium having potassium carbonate and thiophenol.

In various embodiments, the starting material is an amino acid selected from the group which includes of alanine, glycine, and valine. In some embodiments the obtained PNA monomer is chiral or achiral.

In various embodiments, to obtain a PNA monomer a nucleobase is added by a condensation reaction between a modified nucleobase and a compound of formula (V). The nucleobase used is a modified nucleobase which is thymine-1-acetic acid.

BRIEF DESCRIPTION OF THE DRAWINGS

The invention has other advantages and features which will be more readily apparent from the following detailed description of the invention and the appended claims, when taken in conjunction with the accompanying drawings, in which:

DETAILED DESCRIPTION OF THE EMBODIMENTS

While the invention has been disclosed with reference to certain embodiments, it will be understood by those skilled in the art that various changes may be made and equivalents may be substituted without departing from the scope of the invention. In addition, many modifications may be made to adapt to a particular situation or material to the teachings of the invention without departing from its scope.

Throughout the specification and claims, the following terms take the meanings explicitly associated herein unless the context clearly dictates otherwise. The meaning of "a", "an", and "the" include plural references. The meaning of "in" includes "in" and "on." Referring to the drawings, like numbers indicate like parts throughout the views. Additionally, a reference to the singular includes a reference to the plural unless otherwise stated or inconsistent with the disclosure herein.

The word "exemplary" is used herein to mean "serving as an example, instance, or illustration." Any implementation described herein as "exemplary" is not necessarily to be construed as advantageous over other implementations. The ingredients are indicated to be in weight % throughout this specification.

Figure 2A:
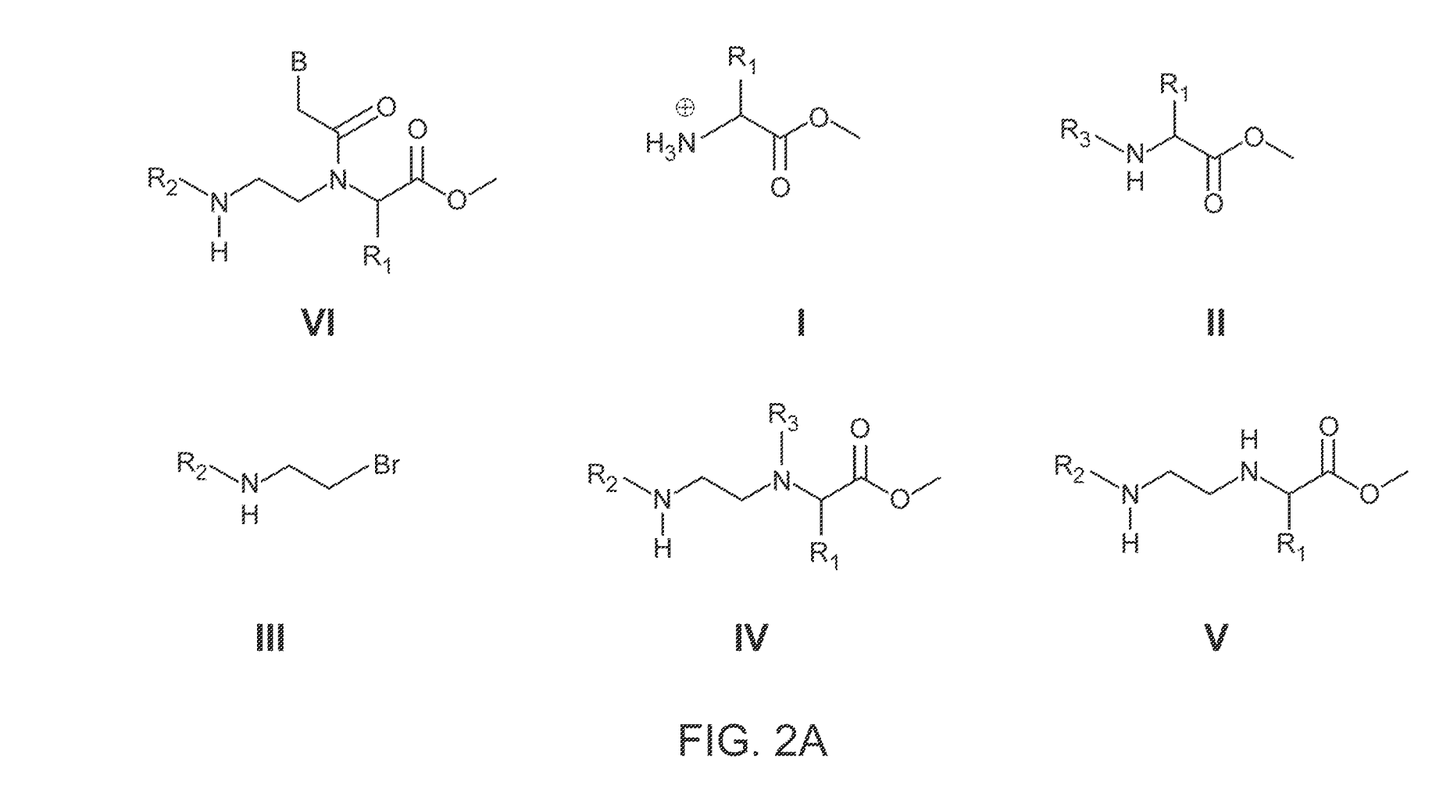
FIG. 2A illustrates starting materials, intermediates and products obtained during the process.

In various embodiments a process 100 for preparing a peptide nucleic acid (PNA) monomer is disclosed. The PNA monomer is of formula (VI) as shown in FIG. 2A.

(VI)

Figure 1:
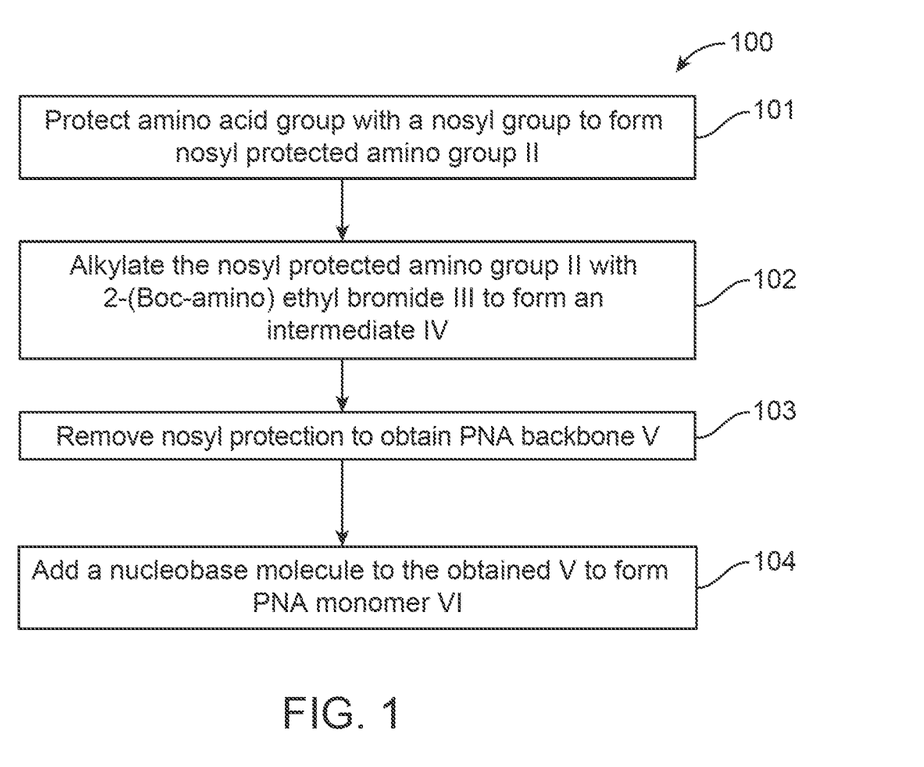
FIG. 1 illustrates a method of preparing a peptide nucleic acid (PNA) monomer.

In one embodiment of the invention the process 100 for preparing a peptide nucleic acid (PNA) monomer is illustrated in four steps 101-104 of FIG. 1. An amino acid (I) is protected with a nosyl group in a nosylation step 101 to form a nosyl protected amino acid (II). The nosyl protected amino acid (II) reacts with a 2-(Boc-amino)ethyl bromide (III) to form an intermediate (IV) as shown in an alkylation reaction step 102. In the next step 103, removal of the nosyl protection group in (IV) results in formation of a PNA backbone (V). In the final step 104, a nucleobase molecule is reacted with the previously obtained PNA backbone (V) to form the PNA monomer (VI) as shown in a condensation reaction 104.

(I)

(II)

(III)

(IV)

(V)

In various embodiments $R_1$ is H or amino acid side chain such as —$CH_3$, —$CH(CH_3)_2$, —$CH_2CH(CH_3)_2$, —$CH_2$—OH, —$CH_2$-ϕ-OH which is either aliphatic hydrocarbon or substituted aliphatic hydrocarbon. In some embodiments, $R_2$ represents an amine protecting group which may be o-nosyl (2-nitrobenzenesulfonyl) or p-nosyl (4-nitrobenzenesulfonyl). In another embodiment of the disclosure, B is a modified nucleobase, and the nucleobase may be thymine, adenine, guanine or cytosine.

Figure 2B:
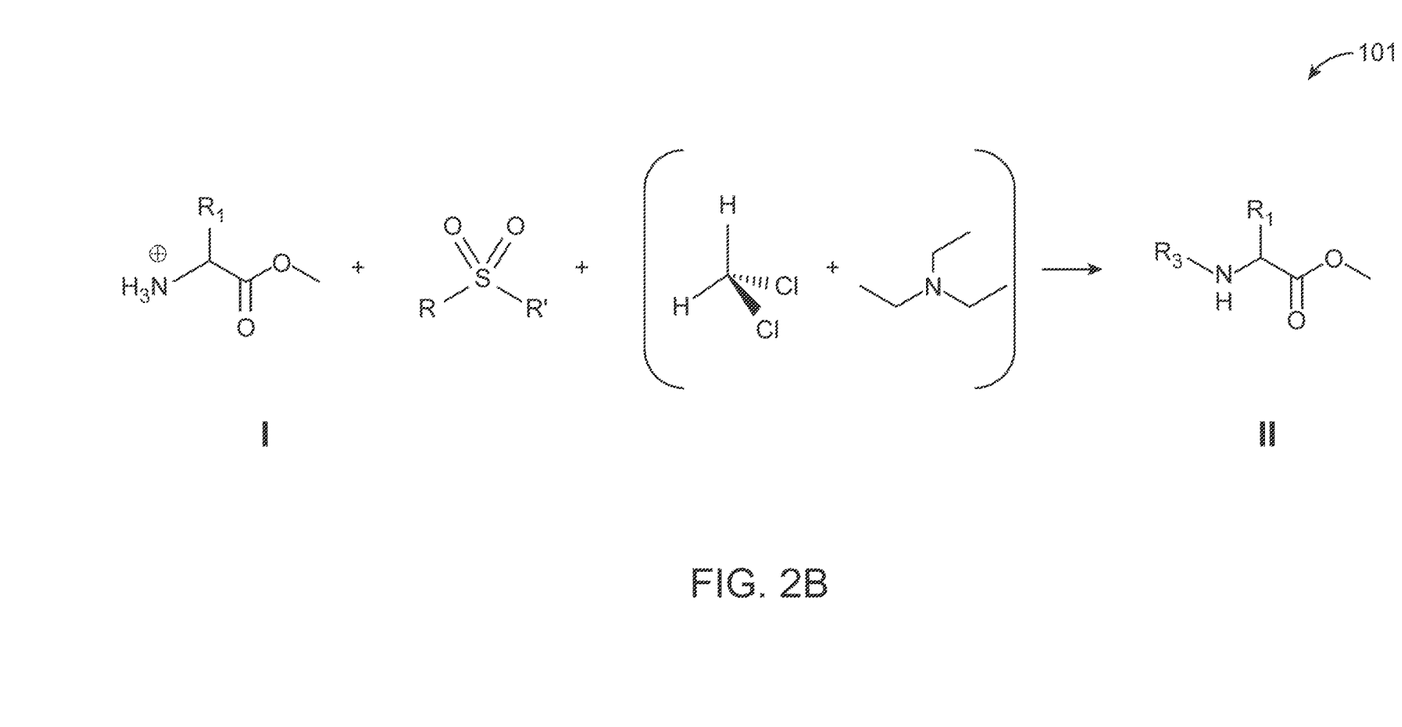
FIG. 2B illustrates nosyl protection of the amino acid.

In one other embodiment, nosylation of the amino acid 101 to protect nitrogen of the amino acid (I) includes reacting an amino acid (I) with nosyl chloride using dichloro methane as solvent in the presence of triethyl amine or diisopropyl ethylamine as a base as shown in FIG. 2B. The reaction is performed at 0-35° C. upon continuous stirring for 20-30 h to form the reaction product with a good yield.

Figure 2C:
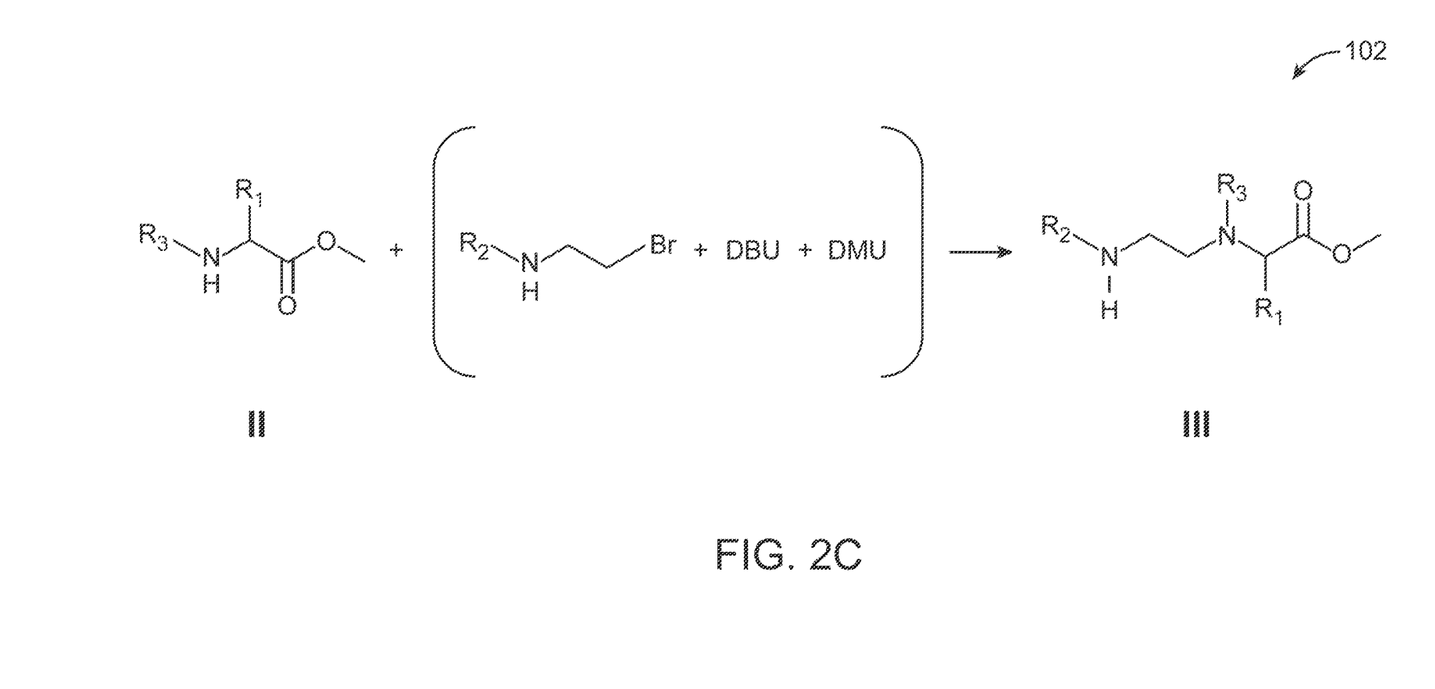
FIG. 2C illustrates alkylation reaction of the nosyl protected amino acid.

In some embodiments, alkylation reaction step 102 of the nosyl-protected amino acid (II) and bromoethylamine (III) to form an intermediate (IV) takes place in a slightly alkaline medium in the presence of cesium carbonate or 1,8-diazabicyclo[5.4.0] undec-7-ene (DBU) or potassium carbonate or triethyl amine as base in dry dimethylformamide (DMF) or acetonitrile solvent as shown in FIG. 2C. The reaction mixture is stirred for a period of about 10-24 h at a temperature between 25-40° C. The intermediate (IV) is obtained after purification using column chromatography.

Figure 2D:
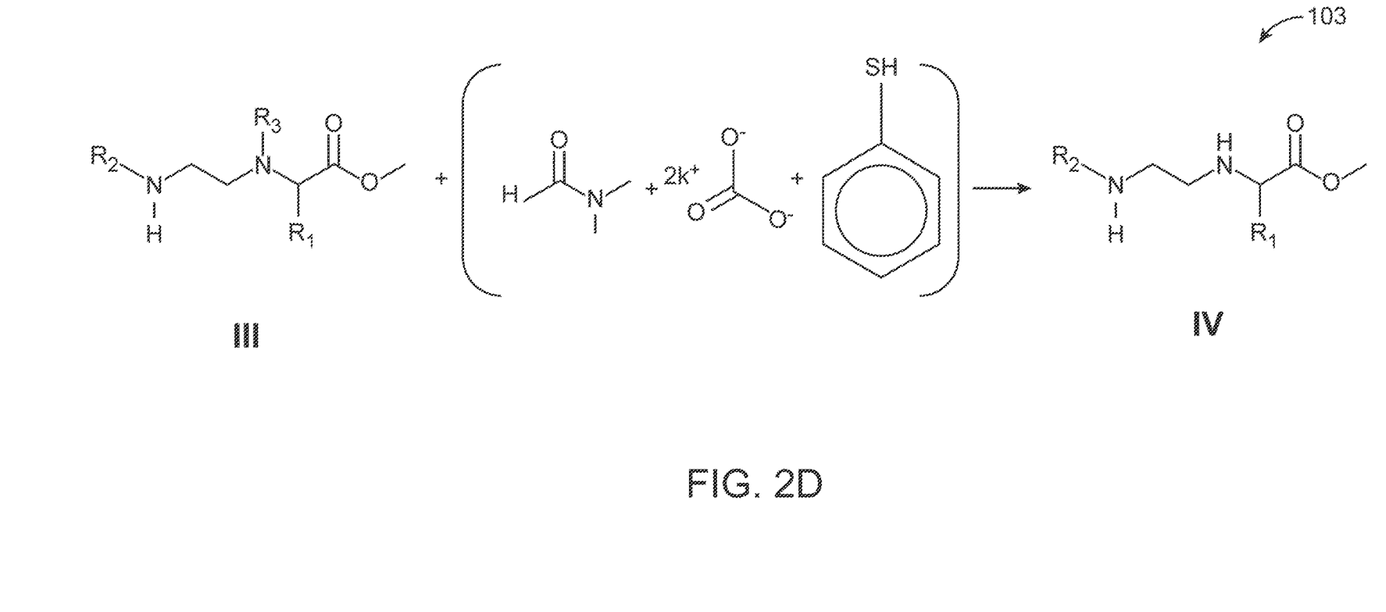
FIG. 2D illustrates removal of the noysl group.

In various embodiments, removal of nosyl protection step 103 comprises reaction with a third reaction mixture which contains a DMF medium comprising of potassium carbonate and thiophenol. The reaction is carried out under nitrogen atmosphere at 0° C. and stirring at 20-30° C. for a period of 15-20 h to obtain the PNA backbone (V) as shown in FIG. 2D.

Figure 2E:
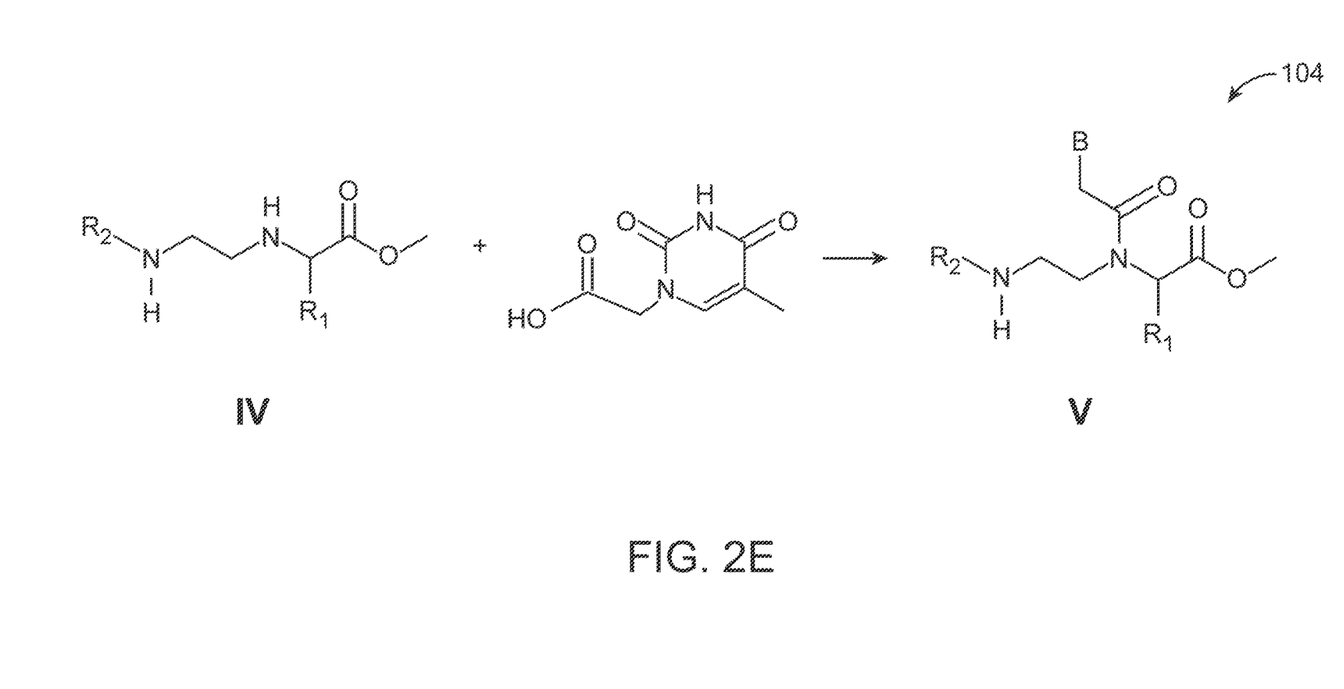
FIG. 2E illustrates addition of a nucleobase to form a PNA monomer.
Figure 2F:
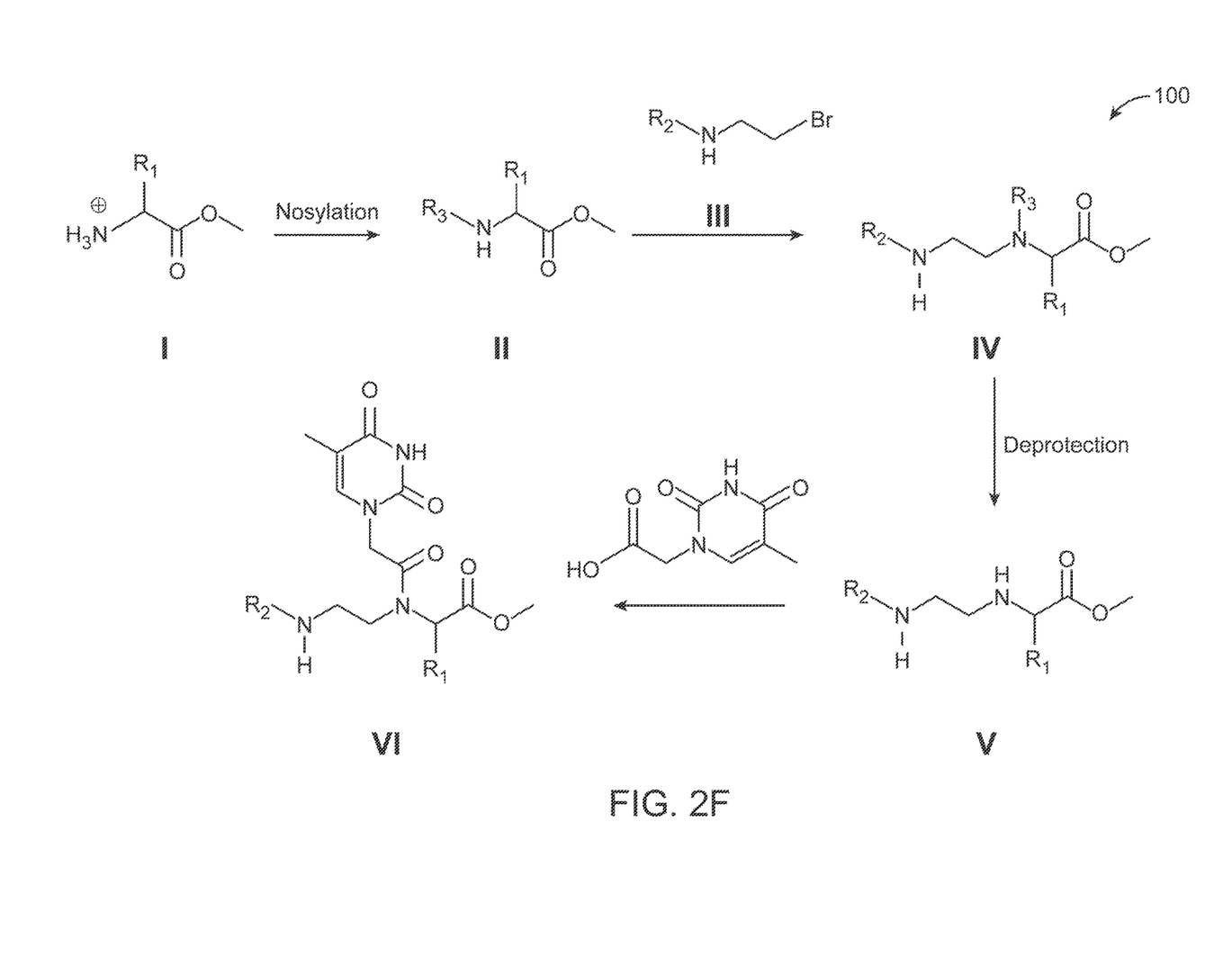
FIG. 2F illustrates a complete reaction to form a PNA monomer from an amino acid starting material.

In various embodiments condensation reaction step 104 comprises a condensation between a modified nucleobase and PNA backbone (V) to form PNA monomer (VI). The modified nucleobase in one embodiment is thymine-1-acetic acid for the synthesis of PNA monomer (VI) as shown in FIG. 2E.

In various embodiments the starting material is an amino acid (I) selected from any one of alanine, glycine, and valine. The amino acid is further modified. In various embodiments the obtained PNA monomers may exhibit either chiral or achiral geometric properties. In one embodiment where $R_1$ is H, the PNA monomer is achiral. In embodiments where $R_1$ is one of $\square CH_3$, $-CH(CH_3)_2$, $\square CH_2CH(CH_3)_2$, $\square CH_2OH$, or $\square CH_2C_6H_5OH$, the PNA monomer is configured to be chiral.

The improved process disclosed yields PNA monomer in four steps by using commercially available cheaper raw materials.

While the invention has been disclosed with reference to certain embodiments, it will be understood by those skilled in the art that various changes may be made and equivalents may be substituted without departing from the scope of the invention. In addition, many modifications may be made to adapt to a particular situation or material the teachings of the invention without departing from its scope. Further, the examples to follow are not to be construed as limiting the scope of the invention which will be as delineated in the claims appended here.

EXAMPLES

Example 1: Protection of Amino Acid Using 4-Nitrobenzenesulfonyl Chloride

The process for one embodiment as shown in FIGS. 1 and 2B to a solution of (I) in DCM 10 ml was added DIPEA followed by o-nosyl-Cl at a temperature between 0° to 5° C. The reaction mixture was stirred at room temperature for 16 h. The reaction was monitored by thin layer chromatography (TLC). After the completion of the reaction the reaction mixture was diluted with DCM (10 ml) and was washed with water (two times) brine solution, dried with $Na_2SO_4$ and further filtered. The resultant residue, after distilling out solvent, was purified by flash chromatography using MeOH-DCM (0-10%) yielded compound (II).

If $R_1$=H; physical properties: Nature: brown solid, yield: 72%, $^1$HNMR (500 MHz, $CDCl_3$) δ: 1.17 (s, 3H), 4.05 (s, 2H), 6.04 (broad singlet, NH), 7.72-7.76 (m, 2H), 7.93-7.95 (m, 1H), 8.09-8.11 (m, 1H). $^{13}$CNMR: 43, 60, 124.33, 129.721, 132.661, 133.438, 134.002, 147.291, 168.888. IR: 1737.86 (C=O), 3334.92 (NH). HRMS: 297.0150 (M+Na), 298.0177 (M+Na+1), 299.0124 (M+Na+2). HPLC purity: 92%, melting point: 84-88° C. (Uncorrected).

If $R_1$=$CH_3$, Nature: colourless solid, $^1$HNMR (500 MHz, $CDCl_3$) δ: 1.481-1.545 (m, $CHCH_3$), 3.520 (s, 3H), 4.230-4.282 (q, CH, 1H), 6.080-6.107 (d, 1H, NH, exchanges with $D_2O$), 7.720-7.752 (m, 2H), 7.919-7.949 (m, 1), 8.074-8.104 (m, 1H). $^{13}$CNMR: 18.081, 51.331, 51.972, 124.184, 129.628, 132.501, 133.288, 134.019, 147.231, 171.814. IR: 1737.86 (C=O), MS: 289 (M+H), 306 (M+$NH_4$). HPLC purity: 98.5%, melting point: 73-77° C. (Uncorrected).

If $R_1$=$CH(CH_3)_2$, physical properties: Nature: viscous oil, yield: 70%, $^1$HNMR (500 MHz, $CDCl_3$) δ: 0.841 (s, 6H), 2.034-2.074 (m, 1H), 3.451 (s, 3H), 3.747 (s, 1H), 7.833-7.883 (m, 2H), 7.918-7.929 (m, 1H), 8.014-8.032 (m, 1H), 8.685 (broad singlet, 1H). $^{13}$CNMR: 17.924, 18.756, 30.239, 51.717, 61.438, 123.912, 129.865, 132.239, 132.833, 134.059, 147.184, 170.916. IR: 1739.79 (C=O), 3321.42 (NH), 1433.90, 1355.96 ($NO_2$), MS (ESI+ve): 317.1 (M+1), 334.2 (M+$NH_4$), 416.2 (M+iso-prop+1); (ESI−ve): 317.1 (M+1), 316.1 ($M^+$), 315.1 M−1), 289 (M+1H), 306 (M+$NH_4$). HPLC purity: 94.2%.

If $R_1$=$CH_2OH$, physical properties: Nature: white solid, yield: 68%, $^1$HNMR (500 MHz, DMSO-d6) δ: 3.502 (s, 3H), 3.615-3.703 (m, 2H), 4.019-4.065 (1H), 5.161-5.190 (t, 1H), 7.832-7.883 (m, 2H), 7.936-7.968 (m, 1H), 8.042-8.065 (m, 1H), 8.561 (s, 1H). $^{13}$CNMR: 51.967, 58.279, 61.932, 124.184, 129.841, 132.496, 133.219, 134.048, 147.244, 170.063. IR: 1743.65 (C=O), 3282.84 (NH), 1450.47, 1365.60 ($NO_2$), MS: 305.1 (M+1), 322.1 (M+$NH_4$), 631.1 (2M+Na). HPLC purity: 95.302% melting point: 112-116° C. (uncorrected).

Example 2: Alkylation of III with II

In another embodiment, to a solution of (II) in DMF was added DBU followed by (III) at room temperature. At room temperature the reaction mixture was stirred for about 16 h, the reaction of which was monitored by TLC. The reaction mixture was diluted with water and extracted with ethyl acetate, dried with $Na_2SO_4$ and further filtered. The resultant residue, after distilling out solvent, was purified by flash chromatography using ethyl acetate-petroleum ether (0-40%) which yielded compound (IV). The same reaction was executed using potassium carbonate instead of DBU and acetonitrile instead of DMF, and the same result was observed.

If $R_1$=H; physical properties: Nature: Yellow viscous oil, yield: 24%, $^1$HNMR (500 MHz, $CDCl_3$) δ: 1.073-1.109 (t, 3H), 1.352 (s, 9H), 3.091-3.135 (q, 2H), 3.322-3.399 (t, 2H), 3.983-4.036 (t, 2H), 4.232 (s, 2H), 6.738-6.764 (broad singlet, NH), 7.820-7.870 (m, 2H), 7.885-7.996 (m, 1H), 8.056-8.079 (m, 1H). $^{13}$CNMR: 13.782, 28.120, 47.499, 48.019, 60.822, 77.830, 124.14, 130.069, 131.669, 132.379, 134.490, 147.339, 155.448, 168.444, IR: 1755.22 (C=O), 1687.71 (C=O), 3321.42 (NH). MS: 454.1 (M+Na), 322.1 (M-Boc), HPLC purity: 98%.

If $R_1$=$CH_3$, physical properties: Nature: colourless viscous oil, yield: 30%, $^1$HNMR (500 MHz, DMSO-d6) δ: 1.326 (s, 9H), 1.326-1.386 (d, 3H), 3.058-3.149 (m, 3H), 3.260 (s, 1H), 3.310-3.365 (m, 3H), 4.576-4.631 (q, 1H), 7.835-7.899 (m, 2H), 7.919-7.946 (m, 1H), 7.969-8.077 (m, 1H). $^{13}$CNMR: 16.133, 28.142, 44.836, 52.180, 55.579, 77.855, 124.146, 130.193, 131.150, 132.264, 134.644, 147.379, 155.544, 171.030. IR: 1703.14 (C=O), MS (−ve mode): 430.1 (M−1), 466.1 (M+Cl), 476.1 (M+ formic acid-H). HPLC purity: 93.8%.

If $R_1$=$CH(CH_3)_2$, physical properties: Nature: colourless solid, yield: 35%, $^1$HNMR (500 MHz, DMSO-d6) δ: 0.882-0.918 (m, 6H), 1.378 (s, 9H), 2.133 (broad singlet, 1H), 3.158-3.177 (m, 2H), 3.337-3.347 (m, 4H), 3.367-3.464 (m, 1H), 3.509-3.928 (m, 1H), 6.947-6.657 (m, 1H), 7.848-8.025 (m, 4H). $^{13}$CNMR: 18.99, 19.49, 28.14, 44.79, 51.73, 65.14, 77.83, 124.05, 130.27, 130.48, 132.15, 134.96, 147.54, 155.51, 169.92. IR: 1714.72 (C=O), 3431.36 (NH), MS: 459.2 (M+), 482.2 (M+Na). HPLC purity: 95%. Melting point: 93-97° C. (Uncorrected).

Example 3: Deprotection of Nosyl Group to Yield V

In another embodiment, to a solution of compound (IV) was added potassium carbonate followed by thiophenol at 0° C. The reaction mixture was stirred at RT for 16 h; the reaction was monitored by TLC. The reaction mixture was diluted with water extracted with ethyl acetate dried with Na₂SO₄ and further filtered. The resultant residue, after distilling out solvent, was purified using flash chromatography with methanol-DCM (0-10%) yielding compound (V).

If R₁=H; physical properties: Nature—Yellow viscous oil, yield: 35%, ¹HNMR (500 MHz, DMSO-d6) δ: 1.35 (s, 9H, CH₃-Boc); 1.65 (s, 1H, CH₂NHCH₂); 2.63-2.67 (t, 2H, CH₂CH₂NHBoc); 3.09-3.15 (q, 2H, CH₂NHBoc); 3.33 (s, 2H, CH₂COOMe); 3.64 (s, 3H, OCH₃); 5.15 (bs, 1H, NH-Boc).

If R₁=CH₃; physical properties: Nature—Yellow viscous oil, yield: 40%, ¹HNMR (500 MHz, CDCl₃) δ: 1.288-1.306 (d, 3H), 1.448 (s, 9H), 2.564-2.622 (m, 1H), 2.738-2.784 (m, 1H), 3.118-3.181 (m, 2H), 3.250-3.372 (q, 1H), 3.724 (s, 3H), 4.973 (broad singlet, 1H). ¹³CNMR: 18.512, 20.188, 46.828, 51.302, 55.634, 77.428, 128.644, 128.763, 131.387, 131.490, 155.568, 175.402. IR: 1705.07 (C=O), 3354.21 (NH), MS: 247.2 (M+1), 248.2 (M+2).

If R₁=CH(CH₃)₂; yield: 52%, ¹HNMR (500 MHz, CDCl₃) δ: 0.926-0.998 (d, 6H), 1.45 (s, 9H), 1.89-1.98 (m, 1H), 2.4-2.6 (m, 1H), 2.7-2.8 (m, 1H), 2.9-3.0 (d, 1H), 3.12-3.3 (m, 2H), 3.7 (s, 3H), 4.9-5.0 (m, 2H), 6.4 (broad singlet, 1H). IR: 1724.36 (C=O), 3336.85 (NH), MS: 275.2 (M+1), 275.2 (M+2).

Example 4: Condensation of Thymine Acetic Acid with V

In another embodiment, to a solution of (V) in dry DMF, carboxymethyl thymine, hydroxyl-1,2,3-benzotriazin-4(3H)-one (DhBtOH) and diisopropylethylamine (DIPEA) were added at room temperature. The reaction mixture was cooled to 0° C. and 1-3-ethylcarbodiamide hydrochloride (EDC.HCl) was added in three portions at intervals of 30 min at 0° C. The reaction pH was maintained ~9 by adding portions of DIPEA upon warming to room temperature and was stirred overnight. The solvent, DMF, was distilled on the following day to get thick yellow oil; this was taken up in ethyl acetate (EtOAc) (50 mL) and washed with water (20 mL). The organic phase was washed with 0.3M KHSO₄ solution (2×25 mL), saturated NaHCO₃ solution (20 mL) and followed by saturated brine solution (20 mL). All the aqueous phases were collected and washed with EtOAc (4×30 mL). All the collected organic phases were dried over Na₂SO₄, were further filtered and evaporated to obtain (VI) as a yellow solid. The crude product was recrystallized using absolute ethanol.

Example 5: Crystallization of the Sample

In another embodiment, the obtained yellow solid from example 4 was dissolved in a minimum quantity of ethanol and warmed to 45° C. The solid got partially dissolved and the obtained product was cooled to 0° C. for 4 h. The obtained white solid was filtered and washed with a minimum quantity of chilled ethanol to obtain (VI).

If R₁=H; physical properties: Nature—White solid, yield: 75%, ¹HNMR (CDCl₃,™): 1.43 (s, 9H, CH₃-Boc); 1.9 (s, 3H, CH₃ of T); 3.3-3.33 (t, 2H, CH₂NHBoc); 3.50-3.55 (t, 2H, CH₂CH₂NHBoc); 3.75 (s, 3H, OCH₃); 4.0 (s, 2H, CH₂ T); 4.5 (s, 2H, CH₂COOMe); 6.96 (s, 1H, CH T). Note: all the observed peaks in NMR are rotamers, except for CH₃ of Boc.

If R₁=CH₃, physical properties: Nature: colourless solid, yield: 80%, ¹HNMR (500 MHz, CDCl₃) δ: 1.52 (s, 9H), 1.608-1.624 (d, 3H), 1.914 (s, 3H), 3.28 (s, 3H), 3.295-3.417 (m, 4H), 3.700 (s, 3H), 4.316-4.347 (q, 1H), 5.5 (broad singlet, 1H), 6.939 (s, 1H). MS: 313 (M-Boc). HPLC purity: 94%.

What is claimed is:

1. A process for preparing a peptide nucleic acid (PNA) monomer, comprising:
   a. providing a nosyl-group containing starting material of formula (II):

wherein R₁ is —H, —CH₃, —CH(CH₃)₂, —CH₂CH(CH₃)₂, —CH₂OH, —CH₂C₆H₅OH and R₃ is o-nosyl or p-nosyl;

b. alkylating the starting material with 2-(Boc-amino)ethyl bromide to form an intermediate of formula (IV):

wherein R₂ is an amine-protecting group, and wherein said alkylating comprises reacting the starting material in a second reaction mixture comprising cesium carbonate or 1,8-diazabicyclo[5.4.0]undec-7-ene (DBU), or triethylamine or pyridine or potassium carbonate and dimethylformamide or acetonitrile as solvent;

c. removing the nosyl group to obtain a compound of formula (V):

and
   d. adding a nucleobase to obtain the PNA monomer.

2. The process of claim 1, wherein said providing a nosyl-group containing starting material comprises: reacting an amino acid containing a first reaction mixture with nosyl chloride to obtain the starting material.

3. The process of claim 2, wherein the first reaction mixture comprises dichloromethane and triethylamine or diisopropylethylamine.

4. The process of claim 2, wherein the reaction is performed at 0-35° C.

5. The process of claim 2, wherein the nosyl product is obtained from stirring the reaction mixture for 20-30 h.

6. The process of claim 1, wherein the alkylation is performed at 25-40° C.

7. The process of claim 1, wherein the alkylation is performed for a period of 10-24 h.

8. The process of claim 1, wherein the intermediate is further purified by column chromatography.

9. The process of claim 1, wherein the removing comprises deprotecting the nosyl group containing a third reaction mixture under nitrogen atmosphere at 0° C. and stirring at 20-30° C. for a period of 15-20 h.

10. The process of claim 9, wherein said reaction mixture comprises a DMF medium comprising potassium carbonate and thiophenol.

11. The process of claim 1, wherein the starting material is an amino acid selected from the group consisting of alanine, glycine, and valine.

12. The process of claim 1, wherein the PNA monomer is chiral or achiral.

13. The process of claim 1, wherein said adding a nucleobase comprises condensation between a modified nucleobase and the compound of formula (V) to obtain the PNA monomer.

14. The process of claim 13, wherein the modified nucleobase is thymine-1-acetic acid.

15. A PNA monomer obtained using the process of claim 1.

* * * * *